(12) United States Patent
Laitinen

(10) Patent No.: US 7,067,700 B2
(45) Date of Patent: Jun. 27, 2006

(54) PROCESS FOR PREPARING SERTRALINE HYDROCHLORIDE POLYMORPHIC FORM II

(75) Inventor: Ilpo Laitinen, Espoo (FI)

(73) Assignee: Fermion Oy, Espoo (FI)

( * ) Notice: Subject to any disclaimer, the term of this patent is extended or adjusted under 35 U.S.C. 154(b) by 129 days.

(21) Appl. No.: 10/479,155

(22) PCT Filed: May 30, 2002

(86) PCT No.: PCT/FI02/00465
§ 371 (c)(1),
(2), (4) Date: Apr. 26, 2004

(87) PCT Pub. No.: WO02/096859
PCT Pub. Date: Dec. 5, 2002

(65) Prior Publication Data
US 2004/0167360 A1    Aug. 26, 2004

Related U.S. Application Data

(60) Provisional application No. 60/294,265, filed on May 31, 2001.

(30) Foreign Application Priority Data
May 31, 2001   (FI) ................................. 20011142

(51) Int. Cl.
*C07C 209/82* (2006.01)
*C07C 209/86* (2006.01)
(52) U.S. Cl. ...................... 564/308; 564/424; 564/437
(58) Field of Classification Search ................. None
See application file for complete search history.

(56) References Cited

U.S. PATENT DOCUMENTS

| 4,536,518 A | 8/1985 | Welch, Jr. et al. |
| 5,248,699 A | 9/1993 | Sysko et al. |
| 5,734,083 A | 3/1998 | Wilson et al. |
| 6,452,054 B1 | 9/2002 | Aronhime et al. |
| 6,495,721 B1 | 12/2002 | Schwartz et al. |
| 6,500,987 B1 | 12/2002 | Schwartz et al. |
| 6,600,073 B1 | 7/2003 | Schwartz et al. |
| 2002/0183555 A1 | 12/2002 | Schwartz et al. |
| 2003/0023117 A1 | 1/2003 | Aronhime et al. |
| 2003/0055112 A1 | 3/2003 | Schwartz et al. |

FOREIGN PATENT DOCUMENTS

| EP | 0 317 131 | 5/1989 |
| JP | 2000 026378 | 1/2000 |
| WO | WO 95/23146 | 8/1995 |
| WO | 00 32551 | 6/2000 |
| WO | WO 00/55157 | 9/2000 |
| WO | WO 01/10441 | 2/2001 |
| WO | 01 32601 | 5/2001 |
| WO | WO 01/45692 | 6/2001 |
| WO | WO 01/72684 | 10/2001 |
| WO | 01 90049 | 11/2001 |
| WO | WO 03/051818 | 6/2003 |

OTHER PUBLICATIONS

J. C. Shan, et al., Drug Development and Industrial Pharmacy, vol. 25, No. 1, pp. 63–67, "Metastable Polymorph of Etoposide With Higher Dissolution Rate", 1999.

*Primary Examiner*—Brian Davis
(74) *Attorney, Agent, or Firm*—Oblon, Spivak, McClelland, Maier & Neustadt, P.C.

(57) ABSTRACT

Sertraline hydrochloride, (1Scis)-4-(3,4-dichlorophenyl)-1,2,3,4-tetrahydro-N-methyl-1-naphtalenaminehydrochloride, polymorph II is prepared by extracting or dissolving the sertraline base into ethyl acetate, adding isopropanol as a solvent, adding hydrogen chloride dissolved in ethyl acetate or in gaseous form, and finally isolating and drying sertraline hydrochloride polymorphic form II.

15 Claims, No Drawings

PROCESS FOR PREPARING SERTRALINE HYDROCHLORIDE POLYMORPHIC FORM II

The present application is a 371 application of PCT/FI02/00465 filed May 30, 2002 and claims the benefit of U.S. provisional application No. 60/294,265 filed May 31, 2001.

The present invention relates to a novel method for the preparation of sertraline hydrochloride, (1S-cis)-4-(3,4-dichlorophenyl)-1,2,3,4-tetrahydro-N-methyl-1-naphtalenamine hydrochloride, polymorph II.

Sertraline has the following structure:

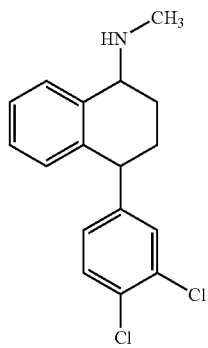

Sertraline is marketed in the form of its hydrochloride for the treatment of depression, obsessive-compulsive disorder and panic disorder.

Synthesis of sertraline is described in U.S. Pat. No. 4,536,518. In a later patent, U.S. Pat. No. 5,248,699, the product of the process described in U.S. Pat. No. 4,536,518 has been defined as polymorphic form II. It has been prepared by treating an ethyl acetate/ether solution of the free base with gaseous hydrogen chloride. U.S. Pat. No. 5,248,699 describes five polymorphic forms of sertraline hydrochloride, differing from one another in respect of their physical properties. The forms are designated form I, form II, form III, form IV and form V. In U.S. Pat. No. 5,734,083 there is described a further polymorphic form of sertraline hydrochloride, designated T1. This polymorph is claimed to be acceptable stable and it has enhanced solubility in aqueous fluids. It is characterized by X-ray diffraction data, X-ray powder diffraction pattern, IR spectrum and unit cell measures. Still further polymorphic forms, designated forms VI to X, and methods for their preparation are described in WO 00/32551. These new forms are characterised by x-ray powder diffraction data and some of them also by IR absorption and differential scanning calorimetry data. Also preparation methods for the previously mentioned polymorphic forms I to V are described.

DESCRIPTION OF THE INVENTION

The present invention relates to a novel method for preparing sertraline hydrochloride polymorphic form II in a repeatable and practical manner. Form II is commercially the most practical form of sertraline polymorph to be used in pharmaceutical formulations. Form I is more stable, but it is not so useful due to its poor dissolution properties. Polymorphic form T1 dissolves better than forms I and II, but it seems to be nearly amorphic and accordingly its processing is difficult, both the preparation of the polymorph and its processing to a tablet.

Another aspect of the present invention is a pharmaceutical composition comprising sertraline hydrochloride polymorphic form II prepared by the method of the invention.

The present invention provides a method for the preparation of sertraline hydrochloride polymorphic form II by a process comprising:
(a) extracting or dissolving the sertraline base into an organic solvent to obtain a first solution comprising sertraline and said organic solvent;
(b) adding isopropanol to said first liquid to obtain a second solution comprising sertraline and isopropanol; and
(c) adding gaseous HCl or HCl dissolved in ethyl acetate while controlling the addition rate to obtain a suspension comprising crystals of sertraline hydrochloride polymorphic form II.

In the process of the invention sertraline base is extracted with or dissolved in ethyl acetate, or some other suitable poorly water soluble organic solvent, e.g. ethylpropionate or isopropylacetate. Most preferably, the organic solvent is ethyl acetate.

The sertraline which is used as the starting material may be the free base of sertraline. Alternatively, it is possible to start with an acid addition salt of sertraline. In this case, it may be preferred to add suitable base to the sertraline salt-organic solvent mixture to liberate the free base of sertraline. Suitable bases include ammonium hydroxide, potassium hydroxide, and sodium hydroxide. Sodium hydroxide is preferred.

When an addition salt of sertraline is neutralized with a base, a water phase containing the salt of the acid may be formed. In this case the water phase is removed by any suitable liquid-liquid separation method, prior to the addition of isopropanol.

Typically, the volume of the resulting solution is then reduced. The reduction of the volume of the solution may be effected by any suitable technique, such as rotary evaporation or distillation. Distillation is preferred and may be carried out at either atmospheric or reduced pressure. The ethyl acetate can also be distilled off totally. During the distillation also the remaining traces of water are removed.

After the volume of the sertraline-organic solvent has been reduced, isopropanol, which is used as a crystallization solvent, is added. The proportion of isopropanol added is typically sufficient to result in a volume ratio of isopropanol to ethyl acetate of from about 100:0 to about 50:50, preferably from 90:10 to 65:35 and the amount of sertraline base to isopropanol is in the range from 0.05 g/ml to 0.2 g/ml.

To the resulting isopropanol solution is then gradually, controlling the addition rate, added 1.0 to 3.0 equivalents, preferably 1.1 to 1.6 equivalents, based on the sertraline present in the isopropanol solution, of non aqueous HCl. Preferably, the HCl is dissolved in ethyl acetate. Typically, the concentration of HCl dissolved in ethyl acetate is from about 10 w/v % to about 25 w/v %, preferably from about 14 w/v % to about 16 w/v %. The HCl dissolved in ethyl acetate is suitably added to the isopropanol solution at a temperature of from 20 to 80° C., preferably from 30 to 55° C. The addition is performed smoothly in about 30 minutes.

Alternatively, hydrogen chloride in gaseous form can be added. In this case, the number of equivalents of HCl and the temperature and time of addition are the same as when using HCl dissolved in ethyl acetate.

In a preferred embodiment, seed crystals of polymorphic form II, may be used to promote the crystallization. The seed crystals, if used, are added during the HCl addition.

The resulting solution is then cooled to a temperature of about 0° C., to obtain a mixture which contains crystals of sertraline hydrochloride form II. The sertraline hydrochloride form II so-produced is then collected by any suitable solid-liquid separation technique, such as filtration, centrifugation, and decantation. Filtration is preferred.

The thus-obtained crystals of sertraline hydrochloride form II may be washed with ethyl acetate. The product may then be dried. A preferred technique is drying under vacuum while raising the temperature slowly to about 80 to 90° C. The product of the process is sufficiently pure so that further purification steps are not necessary.

The sertraline hydrochloride polymorph form II prepared by the method described is stable.

Pharmaceutical compositions containing sertraline hydrochloride polymorphic form II prepared by the method of the present invention can be prepared by methods known in the art.

Other features of the invention will become apparent in the course of the following descriptions of exemplary embodiments, which are given for illustration of the invention and are not intended to be limiting thereof.

EXAMPLE 1

Sertraline Hydrochloride, Polymorphic Form II (1S-cis)-4-(3,4-dichlorophenyl)-1,2,3,4-tetrahydro-N-methyl-1-naphtalenamine, mandelic acid salt (40 g), ethyl acetate (380 ml) and water (360 ml) are charged. 50% NaOH (20 ml) is added at about 65° C. The water phase is separated off. The ethyl acetate solution is washed with water (100 ml). Ethyl acetate (180 ml) is added to the ethyl acetate phase. Most of the ethyl acetate is distilled off, the volume of the distillation residue is 100 ml. Isopropanol (280 ml) is added. Activated charcoal is added and the mixture is stirred for 10 minutes. The solution is filtered. Hydrogen chloride 14% in ethyl acetate (36 ml of the solution) is added smoothly at 40° C. in 30 minutes. Seed crystals of polymorphic form II are added during the addition of HCl. The solution is cooled to 0° C. The crystalline compound is filtered and washed with ethyl acetate (60 ml). The product is dried under reduced pressure raising the temperature gradually to 80–90° C. The yield of sertraline hydrochloride polymorph II is 25.9 g (87%).

EXAMPLE 2

Sertraline Hydrochloride, Polymorphic Form II (1S-cis)-4-(3,4-dichlorophenyl)-1,2,3,4-tetrahydro-N-methyl-1-naphtalenamine, mandelic acid salt (10 g), ethyl acetate (95 ml) and water (90 ml) are charged. 50% NaOH (5 ml) is added at 65° C. The water phase is separated off. The ethyl acetate solution is washed with water (25 ml). Ethyl acetate (45 ml) is added to the ethyl acetate phase. The ethyl acetate is distilled off under reduced pressure. Isopropanol (80 ml) is added. The solution is filtered. Hydrogen chloride 12% in ethyl acetate (12 ml of the solution) is added smoothly at 60° C. in about 20 minutes. Seed crystals are added during the addition. The solution is cooled to 0° C. The crystalline compound is filtered and washed with ethyl acetate (60 ml). The product is dried under reduced pressure raising the temperature gradually to 80–90° C. The yield of sertraline hydrochloride is 6.7 g (89%).

The invention claimed is:

1. A process for preparing sertraline hydrochloride polymorphic form II comprising:
   (a) extracting or dissolving at least one of a sertraline base and an acid addition salt of sertraline into an organic solvent to obtain a first solution;
   (b) adding isopropanol to said first solution to obtain a second solution;
   (c) adding gaseous HCl or HCl dissolved in ethyl acetate while controlling the addition rate to obtain a suspension comprising crystals of sertraline hydrochloride polymorpic form II; and
   (d) isolating sertraline hydrochloride polymorphic form II.

2. The process according to claim 1 wherein the organic solvent is ethyl acetate.

3. The process of claim 1, wherein an acid addition salt is extracted or dissolved in the organic solvent and wherein the method further comprises adding a base to said first solution; and removing any water phase formed in said first solution prior to adding isopropanol.

4. The process according to claim 1 wherein the sertraline hydrochloride polymorphic form II is washed with ethyl acetate before drying.

5. The process according to claim 1 wherein the sertraline base is extracted from sertraline mandelate.

6. The process according to claim 1 wherein the volume proportion of isopropanol to ethyl acetate is from about 100:0 to about 50:50.

7. The process according to claim 1 wherein the volume proportion of isopropanol to ethyl acetate is from 90:10 to 65:35.

8. The process according to claim 1 wherein the proportion of sertraline base to isopropanol is from 0.05 g/ml to 0.2 g/ml.

9. The process according to claim 3, wherein the base is one or more of ammonium hydroxide, potassium hydroxide, and sodium hydroxide.

10. The process according to claim 9, wherein the base is sodium hydroxide.

11. The process according to claim 1, wherein the volume of the first solution is reduced prior to the addition of isopropanol.

12. The process according to claim 1, wherein HCl dissolved in ethyl acetate is added in (c) and wherein the concentration of HCl dissolved in ethyl acetate is from 10 w/v % to 25 w/v %.

13. The process according to claim 12, wherein the concentration of HCl dissolved in ethyl acetate is from 14 w/v % to 16 w/v %.

14. The process according to claim 1, wherein HCl dissolved in ethyl acetate is added in (c) and wherein the HCl dissolved in ethyl acetate is added at a temperature of form 20 to 80° C.

15. The process according to claim 14, wherein the HCl dissolved in ethyl acetate is added at a temperature of form 30 to 55° C.

* * * * *